United States Patent
McCabe et al.

[11] Patent Number: 5,716,337
[45] Date of Patent: Feb. 10, 1998

[54] ABSORBENT PRODUCT

[75] Inventors: John Patrick McCabe, Skipton; Peter John Stevens, Shipley, both of United Kingdom

[73] Assignee: Johnson & Johnson Medical, Inc., Arlington, Tex.

[21] Appl. No.: 274,658

[22] Filed: Jul. 13, 1994

Related U.S. Application Data

[63] Continuation of Ser. No. 68,354, May 27, 1993, abandoned.

[30] Foreign Application Priority Data

Jun. 10, 1992 [GB] United Kingdom ............ 9212303
Jul. 31, 1992 [GB] United Kingdom ............ 9216285

[51] Int. Cl.⁶ .................. A61F 13/00; A61F 15/00
[52] U.S. Cl. .................. 602/49; 602/42; 602/59; 604/304
[58] Field of Search .................. 602/41, 42, 43, 602/47, 49, 52, 75, 59; 604/364, 368, 385.1, 304, 307, 56, 82, 92, 410, 416

[56] References Cited

U.S. PATENT DOCUMENTS

| | | | |
|---|---|---|---|
| 3,095,877 | 7/1963 | Rowan | 128/260 |
| 3,595,235 | 7/1971 | Jerpersen | 604/364 |
| 3,762,413 | 10/1973 | Hanke | 128/285 |
| 3,814,101 | 6/1974 | Kozak | 604/370 |
| 4,460,642 | 7/1984 | Errede et al. | 602/42 |
| 4,793,337 | 12/1988 | Freeman et al. | 602/49 |
| 5,000,746 | 3/1991 | Meiss | 602/43 |
| 5,002,814 | 3/1991 | Knack et al. | 604/385.1 |
| 5,180,622 | 1/1993 | Berg et al. | 604/368 |
| 5,197,945 | 3/1993 | Cole et al. | 602/42 |

FOREIGN PATENT DOCUMENTS

| | | |
|---|---|---|
| 0 171 268 | 12/1986 | European Pat. Off. |
| 0 344 913 | 6/1989 | European Pat. Off. |
| 2 402 594 | 6/1979 | France. |
| 1 642 146 | 4/1971 | Germany. |

*Primary Examiner*—Paul B. Prebilic
*Attorney, Agent, or Firm*—Andrew C. Farmer; James Riesenfeld

[57] ABSTRACT

A product suitable for absorbing wound exudate comprising a series of interconnected square or rectangular perforated bags made of a substance of maximum thickness 1 mm e.g. film, which is substantially non-adherent to a wound, wherein alginic acid or a salt thereof such as calcium alginate is housed in the bags, preferably in the form of small spheres. The film preferably comprises ethylene/methyl acrylate copolymer. Alternatively, the product comprises a string along which beads of alginic acid or alginate are threaded.

26 Claims, 1 Drawing Sheet

ABSORBENT PRODUCT

This is a continuation of application Ser. No. 08/068,345, filed May 27, 1993 now abandoned.

This invention relates to a product suitable for absorbing fluid from wounds during the healing process.

Various products have been used for absorbing fluids such as wound exudate, but they tend to be fibrous and are therefore prone to adhere to the wound and to leave bits in the wound.

Such difficulties have been overcome by the use of the absorbent product of this invention. This product comprises bits of alginic acid or a salt thereof as an assemblage capable of being applied to the vicinity of a wound to absorb the wound exudate. The form in which the bits are assembled is a string on which the bits are carried directly or perforated bags interconnected by a string in which the bits are housed, which bags are made of a substance of maximum thickness 1 mm which is substantially non-adherent to a wound.

Bits can take various forms. Thus, they can be granules, pellets, spheres or in one specific form beads, i.e. spheres having a hole therethrough, so that they can be strung together. In general, by bit we mean any small discrete quantity which need not be regular in shape and this quantity is usually less than 0.1 gm in weight.

Alginic acid or a salt thereof (hereinafter referred to as "alginate") is extracted from seaweed and consists of linear polysaccharides in which the monomeric units are mannuronic acid and guluronic acid. The alginate which is used may, for example, be calcium alginate, zinc alginate, sodium alginate, barium alginate, ammonium alginate or mixtures thereof. Calcium alginate is particularly preferred and may be prepared by an ion exchange reaction between sodium alginate and calcium chloride.

The alginate may however be in the form of a gel, generally from 0.01 to 2.0 mm in thickness. Such gels may suitably be formed by the controlled introduction of a suitable cation (e.g. calcium) into a solution of a water soluble alginate such as sodium alginate, preferably in the presence of a pH modifier such as glucono delta lactone. The alginate concentration may be, for example, from 2% to 20% by weight and the final cation concentration may suitably be from 0.2% to 10% by weight. The resultant gel will typically contain from 30% to 99% by weight of water, and it may then be partially or completely dried if desired, e.g. to a water content of from 15% to 50%, and more preferably from 20% to 40% by weight.

The assemblage of bits can be of various constructions. Thus, in one form the bits of alginate are housed in a perforated bag made of a thin substance so that in use the exudate from the wound passes through the perforations where it is absorbed by the alginate, for example as pellets, spheres or granules which thereby swell when absorbing the exudate.

In another form the assemblage comprises a string along which beads of alginate are threaded. A suitable length of the string is then placed adjacent to the wound and when the exudate is absorbed by the beads they swell.

In all cases the assemblage is preferably sterile packaged.

When the alginate is housed in a perforated bag the substance from which the bag is made should be of maximum thickness 1 mm, preferably less than 0.5 mm. The substance should also be substantially non-adherent to a wound.

Although the alginate can be housed in just one perforated bag it is preferred that it be housed in a series of interconnected perforated bags.

The bag or bags are preferably made of a film, i.e. any suitable material of thickness less than 300 micrometers, for example from 20 to 100 micrometers thick, and preferably from 30 to 70 micrometers thick, e.g. about 60 micrometers.

Each bag which contains alginate should be perforated. These perforations should be of sufficient size to allow wound exudate to penetrate, but not so large that substantial portions of the alginate can drop out of the bag. Preferably the alginate is used in the form of small dry spheres, and particularly spheres having a diameter of 0.5 mm to 1.5 mm, for example 1 mm. By "sphere" we do not mean that it has to be a geometrically perfect sphere and could include granules if not too irregular.

The perforations in the bags should have dimensions less than the diameter of such spheres. Typical perforations are squares with sides of 0.5 to 1.00 mm length, e.g. about 0.8 mm.

The amount of alginate in each bag can vary but amounts of from about 1.5 mg to 100 mg per bag are suitable. When the alginate is in the form of spheres each bag preferably has from 1 to 50 spheres, especially from 28 to 32 spheres, e.g. 30 spheres.

The shape of the bags can vary but preferred are substantially rectangular or square bags, preferably of 1 to 5 cm width and 1 to 10 cm length, especially with a width 2 to 3 cm, and length 3 to 4 cm. The depth is preferably about 0.1 cm to 0.4 cm when the alginate is dry.

Alternatively cylindrical bags can be used of length preferably from 1 to 10 cm, especially from 3 to 4 cm. As another alternative, the bags can be for example elliptical cylinders. The diameter of cylindrical bags (or the maximum diameter if the bags are of elliptical section) is preferably from 1 to 5 cm, and more preferably from 2 to 3 cm.

Preferably the series of bags comprises a series of contiguous bags, but this is not essential. The bags are preferably joined to each other side by side, so that the series or line of bags resembles one long flat ribbon. This ribbon is preferably 5 to 30 cm in length and 0.5 to 2.5 cm width.

It is preferred that the bags be connected with a string, thread or cord or similar line running substantially along the length of bags and such a line, e.g. string, thread or cord, is essential when the bags are adjacent to one another but not contiguous with one another. In this case it connects the bags together. Preferably the line runs through each bag and if for example the bags are a series of end-on cuboids or cylinders, the line can run substantially centrally through each cuboid or cylinder, i.e. centrally throughout the length of the ribbon.

The bag or bags must be made of a substance which is substantially non-adherent to the wound, i.e. substantially hydrophobic. Various plastic substances can be used but the preferred plastics is one comprising ethylene/methyl acrylate copolymer and preferably including low density polyethylene. One preferred form comprises 16% by weight of ethylene/methyl acrylate copolymer, 83% by weight low density polyethylene and 1% process additives.

Other suitable plastics materials include water-impermeable polymers, such as a polyolefin. Polyethylene and polypropylene are representative examples of this class, but polymers of higher olefins may of course be used, as may copolymers of two or more olefins, or copolymers of the olefin and one or more other monomers.

Although fibrous plastics material is not preferred because of the risk of portions adhering to the wound it is possible to use such substances if the fibres are fully bonded to one another and there are no loose fibres.

Examples of such fibrous materials which may be used are polyolefins such as polyethylene, polypropylene and polybutylene homopolymers and copolymers, vinyl polymers such as polyvinylchloride, polyamides such as nylon, and polyesters. Other fibres include rayon and acrylic fibres. In particular one can use polyester fibres having a relatively high melting point of approximately 250° C.

To use this form of the product the series of bags, preferably in the form of a ribbon, is fed into the wound. Whilst present in the wound, the alginate preferably as dried spheres, absorbs fluids such as wound exudate, and the alginate if in the form of spheres will swell to produce spheres of diameters of approximately 1 to 3 mm, e.g. about 3 mm. When all the wound exudate has been absorbed the series of bags, e.g. ribbon, now containing hydrated alginate, will be removed and discarded.

When the assemblage comprises a string along which beads of alginate are threaded, the string can be the same or similar to that described above in connection with the bags. The string can be a thin length of cord, thread, twine, fibre or similar material and may be of natural or synthetic material. Thus it may be a nylon thread.

If the beads are spaced at intervals along the string it is preferred that the diameter of the holes in the beads is such that the beads are not too free to slide along the string so that the beads remain spaced apart. A string or fairly course twine having a fairly rough surface, would also be of assistance in this respect. When the beads are spaced apart it is preferred that the average spacing is about the diameter of the bead, e.g. about 3 mm.

If desired the string of beads may be contained in a housing made of thin perforated material. This housing is preferably cylindrical and which preferably houses substantially the whole string of beads. The perforated material from which the housing is made is preferably that described and exemplified above in connection with the perforated bags. In this case however it is not necessary that the perforations are smaller than the diameter of the beads. As before the preferred material for the housing is a plastics comprising ethylene/methyl acrylate copolymer and low density polyethylene.

Also according to this invention, the alginate especially in the form of granules, pellets or spheres may be sprinkled onto the wound to absorb the exudate. They would be allowed to rehydrate before being irrigated away.

In a further embodiment the bits of alginate, e.g., spheres of alginate, could contain active wound healing agents, for example growth factors, collagen, glycosaminoglycans, vitamins, antiseptic agents and enzyme debridiers.

It is preferred that the bags be connected with a string, thread or cord or similar line running substantially along the length of bags. Such a line is essential when the bags are adjacent to one another but spaced apart from, as in not contiguous with, one another.

Specific forms of the invention are described with reference to the drawings in which:-

BRIEF DESCRIPTION OF DRAWINGS

Referring to FIGS. 1 and 2, 1 indicates a series of rectangular contiguous bags 2 sealed at edges 3. Each bag is made of plastics film comprising ethylene methyl/acrylate copolymer and low density polyethylene and each bag perforated with perforations 4 as shown on one of the bags.

Each bag contains approximately 56 mg of calcium alginate spheres of diameter less than or approximately equal to 1 mm when dry. A string 5 runs through each of the bags to facilitate entry and removal of the ribbon from the wound. When the spheres absorb exudate they swell to a diameter of about 3 mm.

Figure 3:
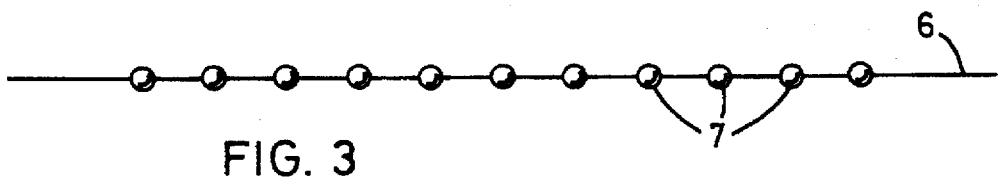
FIG. 3 shows another form of the invention.

Referring to FIG. 3 beads of alginate 7 of approximate diameter 3 mm are threaded onto a string 6 at intervals of approximately 4 mm.

Figure 1:
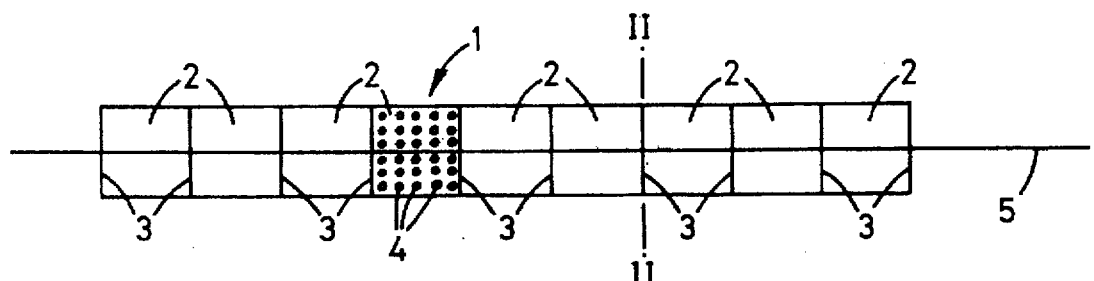
FIG. 1 shows one form of the invention as a section of a ribbon along line I—I of FIG. 2.
Figure 2:
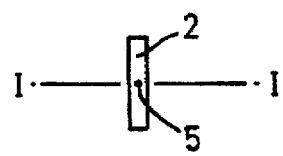
FIG. 2 is a cross-sectional view of the ribbon along line II—II of FIG. 1.

FIGS. 1 and 2 illustrate a first embodiment of a flexible, linearly elongated, absorbent product according to the invention. It comprises a linear series of rectangular contiguous absorbent members which in turn comprise bags 2 containing absorbent material. The absorbent material in each bag 2 comprises approximately 56 mg of calcium alginate spheres of a diameter less than or approximately equal to 1 mm when dry. The bags 2 form containment means for inhibiting release of the absorbent material into a wound. To this end, each bag 2 is made of plastic film which is perforated by perforations 4 and sealed at edges 3 of the bags 2. The film comprises ethylene methyl/acrylate copolymer and low density polyethylene.

The bags 2 are arranged in end-to-end relationship and a flexible linearly elongated carrier means, namely a string 5, runs through each of the bags to facilitate entry and removal of the ribbon from the wound. When the spheres absorb exudate they swell to a diameter of about 3 mm.

Figure 4:
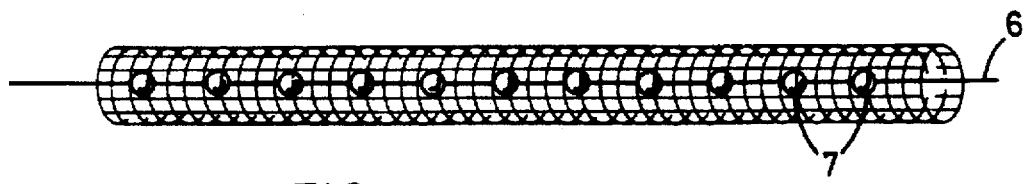
FIG. 4 shows a modification of the invention shown in FIG. 3.

FIGS. 3 and 4 illustrate a second embodiment of a flexible linearly elongated absorbent product according to the invention which comprises a flexible, elongated carrier means, namely a string 6, connecting, in linear series, a plurality of swellable absorbent members, namely beads 7 of an absorbent material comprising alginate. The beads 7 are contained to the product by being directly attached to the string 7 in the form of the string 6 passing through apertures in each of the beads 7. Adjacent beads 7 are spaced apart from each other by approximately 4 mm and the approximate diameter of each bead is 3 mm.

When placed adjacent to a wound the beads of the string of FIG. 3 or of the housed string of FIG. 4 swell as they absorb the exudate.

What is claimed is:

1. A flexible, linearly elongated, absorbent product for absorbing wound exudate, said product comprising a flexible, linearly elongated carrier means and a plurality of swellable absorbent members disposed in series along the carrier means;

said absorbent members comprising bits of alginic acid or a salt thereof;

said carrier means comprising a string connecting perforated bags that house the bits, said perforated bags being made of a substance which is:

(i) no more than 1 mm thick and (ii) substantially non-adherent to a wound.

2. A product according to claim 1 wherein the alginic acid salt is calcium alginate.

3. A product according to claim 1 wherein the carrier means comprises the bags being formed in end to end relationship and wherein the bags are substantially rectangular in shape.

4. A product according to claim 3 wherein the bits are in the form of spheres.

5. A product according to claim 1 wherein the bits of alginic acid or salt thereof contain active wound healing agent.

6. A flexible, linearly elongated, absorbent wound dressing comprising:

a plurality of absorbent members, each absorbent member comprising an absorbent material comprising alginic acid or a salt thereof;

a flexible, elongated connecting member attached to and connecting the absorbent members in linear series; and containment means for inhibiting release of the absorbent material from the wound dressing into a wound.

7. An absorbent wound dressing according to claim 6 wherein the containment means comprises the absorbent members further comprising bags formed of a non-adherent, fluid transmissive substance and wherein the absorbent material is contained within the bags.

8. An absorbent wound dressing according to claim 7 wherein the absorbent material comprises a plurality of bits.

9. An absorbent wound dressing according to claim 8 wherein the bags are perforated and the perforations in the bags are smaller than the bits.

10. An absorbent wound dressing according to claim 7 wherein each of the bags contains from 1.5 mg to 100 mg of the absorbent material.

11. An absorbent wound dressing according to claim 7 wherein the bags are attached to each other in end to end relationship and the connecting member comprises the bags and the end to end relationship of the bags.

12. An absorbent wound dressing according to claim 7 wherein the connecting member comprises a string and the string is separate from the bags.

13. An absorbent wound dressing according to claim 12 wherein the bags are spaced apart from each other on the string.

14. An absorbent wound dressing according to claim 7 wherein the substance of which the bags are formed has a thickness not more than 1 mm.

15. An absorbent wound dressing according to claim 7 wherein the substance of which the bags are formed is hydrophobic.

16. An absorbent wound dressing according to claim 7 wherein the bags are formed of an ethylene/methyl acrylate copolymer.

17. An absorbent wound dressing according to claim 7 wherein the bags are formed of low density polyethylene.

18. An absorbent wound dressing according to claim 6 wherein the containment means comprises the individual absorbent members comprising particles of the absorbent material that are directly attached to the connecting member.

19. An absorbent wound dressing according to claim 18 wherein the individual particles of absorbent material weigh less than 0.1 gm each.

20. An absorbent wound dressing according to claim 18 wherein the connecting member comprises a string.

21. An absorbent wound dressing according to claim 20 wherein the particles comprise spheres having apertures therethrough and the string passes through the apertures.

22. An absorbent wound dressing according to claim 21 wherein the spheres have diameters of from about 0.5 mm to about 3 mm when dry.

23. An absorbent wound dressing according to claim 22 wherein the spheres are spaced apart along the string and adjacent spheres are about 3 mm apart.

24. An absorbent wound dressing according to claim 18 and further comprising tubular enclosure formed of a fluid transmissive non-adherent substance that coaxially receives at least a portion of the connecting member and absorbent members.

25. An absorbent wound dressing according to claim 6 wherein the alginic acid salt is calcium alginate.

26. An absorbent wound dressing according to claim 6 wherein the absorbent members contain an active wound healing agent.

* * * * *